(12) United States Patent
Otani et al.

(10) Patent No.: US 7,479,255 B2
(45) Date of Patent: Jan. 20, 2009

(54) GAS SENSOR

(75) Inventors: Seiichi Otani, Tokyo (JP); Yukio Nakamura, Tokyo (JP); Mamoru Furusato, Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 773 days.

(21) Appl. No.: 10/495,790

(22) PCT Filed: Nov. 14, 2002

(86) PCT No.: PCT/JP02/11875

§ 371 (c)(1),
(2), (4) Date: Nov. 1, 2004

(87) PCT Pub. No.: WO03/042678

PCT Pub. Date: May 22, 2003

(65) Prior Publication Data

US 2005/0042141 A1    Feb. 24, 2005

(30) Foreign Application Priority Data

Nov. 15, 2001 (JP) ............... 2001-350021
Oct. 9, 2002 (JP) ............... 2002-295794
Oct. 9, 2002 (JP) ............... 2002-295795

(51) Int. Cl.
*G01N 31/12* (2006.01)
*G01N 27/16* (2006.01)

(52) U.S. Cl. ............... 422/94; 422/95; 422/96; 422/97; 436/144; 436/159

(58) Field of Classification Search ............... 422/88, 422/90, 94, 95, 96, 97; 436/144, 152, 155, 436/159
See application file for complete search history.

(56) References Cited

U.S. PATENT DOCUMENTS

| | | | | |
|---|---|---|---|---|
| 3,476,517 A | * | 11/1969 | Smith | 422/96 |
| 3,586,486 A | | 6/1971 | Kim et al. | |
| 4,861,557 A | * | 8/1989 | McNally | 422/97 |
| 5,601,693 A | * | 2/1997 | Davies | 204/400 |
| 5,624,641 A | * | 4/1997 | Capetanopolous et al. | 422/98 |
| 5,879,631 A | * | 3/1999 | Wewers et al. | 422/98 |
| 5,902,556 A | * | 5/1999 | Van De Vyver et al. | 422/174 |
| 5,959,190 A | * | 9/1999 | Peinecke et al. | 73/25.01 |
| 6,155,099 A | * | 12/2000 | Kobayashi et al. | 73/31.05 |
| 6,173,602 B1 | * | 1/2001 | Moseley | 73/31.06 |
| 6,284,545 B1 | * | 9/2001 | Warburton et al. | 436/124 |

(Continued)

FOREIGN PATENT DOCUMENTS

EP    0608122    7/1994

(Continued)

*Primary Examiner*—Frank M Lawrence
*Assistant Examiner*—Robert A Clemente
(74) *Attorney, Agent, or Firm*—Connolly Bove Lodge & Hutz LLP

(57) ABSTRACT

A hydrogen sensor 25 has a fitting base plate 29 in which a gas-sensing chamber 34 is formed, a specimen gas intake 35 formed on said fitting base plate 29, opening toward an exit passage 24 and introducing hydrogen gas into the gas-sensing chamber 34, a gas-sensing element 39 held in the gas-sensing chamber 34 and adapted to sense hydrogen gas, and a water-repelling filter 44 covering the specimen gas intake 35.

15 Claims, 17 Drawing Sheets

U.S. PATENT DOCUMENTS

| | | | |
|---|---|---|---|
| 6,344,174 B1 * | 2/2002 | Miller et al. | 422/98 |
| 6,548,024 B1 * | 4/2003 | Doncaster et al. | 422/88 |
| 6,660,231 B2 * | 12/2003 | Moseley | 422/98 |
| 6,663,834 B1 * | 12/2003 | Miller et al. | 422/94 |
| 6,756,016 B2 * | 6/2004 | Miller et al. | 422/98 |
| 6,911,180 B2 * | 6/2005 | Miller et al. | 422/94 |
| 7,329,389 B2 * | 2/2008 | Horovitz et al. | 422/83 |

FOREIGN PATENT DOCUMENTS

| | | |
|---|---|---|
| JP | 62-299753 A | 12/1987 |
| JP | 3-61848 A | 3/1991 |
| JP | 6-223850 A | 8/1994 |
| JP | 7-49324 A | 2/1995 |
| JP | 8-121754 A | 5/1996 |
| JP | 8-201331 A | 8/1996 |
| JP | 9-63610 A | 3/1997 |
| JP | 9-184817 A | 7/1997 |
| JP | 2590271 | 2/1999 |
| JP | 2001-66282 A | 3/2001 |

\* cited by examiner (A)

(B)

(C)

(A)

(B)

(A)

(B)

(C)

(A)

(B)

(C)

(A)

(B)

(C)

(A)

(B)

(C)

GAS SENSOR

TECHNICAL FIELD

This invention relates to gas sensors for use in highly humid environments, and more particularly to the water-repelling and drip-proof structures of such gas sensors.

BACKGROUND TECHNOLOGY

For example, a solid polymer membrane type fuel battery has a stack of multiple cells each of which consists of a membrane of solid polyelectrolyte held between an anode and a cathode. While hydrogen is supplied as a fuel to the anode, air is supplied as an oxidizer to the cathode. Hydrogen ions generated by the catalytic reaction at the anode move through the film of solid polyelectrolyte to the cathode where an electrochemical reaction between the hydrogen ions and oxygen generates electricity.

Fuel batteries like the aforesaid solid polymer membrane type fuel battery generally discharge the unreacted air (hereinafter referred to as the off-gas)to outside the system. Then, it is necessary to confirm that hydrogen gas is not present in the off-gas.

Therefore, systems to confirm the nonpresence of hydrogen gas in the off-gas by means of a hydrogen sensor installed in the discharge system on the cathode side of the fuel battery are proposed, as in Japanese Patent Publication No. 1994-52662 and Japanese Provisional Patent Publication No. 1994-223850.

A contact combustion type gas sensor may be used as the hydrogen sensor. This contact combustion type gas sensor comprises a sensing element carrying a catalyst and a temperature-compensating element carrying no catalyst. This gas sensor determines the concentration of the specimen gas from the difference in electrical resistance between the sensing and temperature-compensating elements by using heat generated when the specimen gas (that is hydrogen when the sensor is a hydrogen sensor) burns on contact with the catalyst.

In order to maintain ion conductivity of the solid polyelectrolyte membrane, the fuel batteries like the aforesaid solid polymer membrane type fuel battery positively moisturize the reacting gas (such as hydrogen or oxygen) supplied to them and produce, when they generate electricity, water of formation by the electrochemical reaction involved in their power generation. Therefore, the off-gas contains heated water and formation water, as a result of which the hydrogen sensor is exposed to the off-gas containing such waters.

As, however, the sensing elements of hydrogen sensors are often gas sensors that work in a heated state like the contact combustion type gas sensors, the heated water or formation water adhering to them creates local nonuniform temperature distribution on the surface thereof that might, in turn, lead to sensitivity lowering and element breakdown.

To eliminate this problem, provision of a gas permeable water-repelling film and aporous silica sheet at the gas intake of containers holding the sensor is proposed, as in Japanese Provisional Patent Publication No. 2000-187014.

Hot and moist fluids, such as those having a temperature of approximately 90° C. and a relative humidity of approximately 100 percent, flow in the off-gas exhaust pipe of fuel batteries like the solid polymer membrane type fuel battery. Provision of a contact combustion type gas sensor that is used in a heated state in such exhaust pipes increases heat-release in the port where the sensor is installed, as a result of which the temperature near the sensor drops to below zero and waterdroplets are formed in the sensor.

To eliminate this problem, the sensor is held in a cap of porous material and heated by a heater provided therearound or temperature drop is prevented by heat insulating material, as proposed in Japanese Provisional Patent Publication No. 1998-233763. However, this solution requires additional work for ancillary facilities for heating or heat insulation, increases installation cost, and hampers size reduction.

The specimen gas may be taken from the exhaust pipe through a sampling passage and led to the sensor through a dehumidifying means. However, this method requires not only large equipment but also correction with moisture amount after removing the measured value. Besides, it also necessitates complex signal processing.

If moisture in the specimen gas adheres and condenses on the porous cap used in the aforementioned prior art, the condensed water comes into contact with the gas-sensing element, thereby creating local nonuniform temperature distribution on the surface of the element that might lead to element breakdown or sensitivity drop.

If the specimen gas flowing in through the cap is not uniformly led to and brought into contact with the sensing and temperature-compensating elements, an imbalance of the flow rate of the incoming specimen gas directly affects the sensing temperature and, thereby, lowers the sensing accuracy.

Keeping the cap that is exposed to and cooled by the flow of the specimen gas at the desired temperature requires a large amount of heat and, thereby, increases power consumption by the gas sensor.

As such, the object of this invention is to provide gas sensors that prevent sensitivity lowering and element breakdown by surely preventing the inflow of the moisture contained in the gas flowing through the fluid path, the wetting of the sensing element and the formation of condensed water in the gas-sensing chamber.

DISCLOSURE OF THE INVENTION

A gas contact combustion type gas sensor of a first invention determines the concentration of the specimen gas from the difference in electric resistance between the sensing and temperature-compensating elements by using the heat generated by the combustion of the specimen gas on contact with a catalyst. This gas sensor also has a water-repelling filter disposed at the specimen gas intake of a case that contains said sensing and temperature-compensating elements and a heater to heat the specimen gas installed between the specimen gas intake and said elements.

While the water-repelling filter prevents the moisture in the specimen gas passage from entering the gas-sensing chamber, the heater directly heats the specimen gas introduced from the specimen gas intake into the gas-sensing chamber. These provisions prevent the adherence of condensed water to the sensing element, thereby preventing sensitivity lowering and element breakdown and, as a result, prolonging the life of the elements.

A gas contact combustion type gas sensor of a second invention determines the concentration of the specimen gas from the difference in electric resistance between the sensing and temperature-compensating elements by using the heat generated by the combustion of the specimen gas on contact with a catalyst. This gas sensor also has a water-repelling filter and a porous metal sheet disposed at the specimen gas intake of a case that contains said sensing and temperature-compensating elements.

While the water-repelling filter prevents the moisture in the specimen gas passage from entering the gas-sensing chamber, the porous metal sheet prevents the sensing element from getting wetted. These provisions prevent element breakdown and sensitivity lowering and prolong the life of the gas sensor.

A gas contact combustion type gas sensor of a third invention determines the concentration of the specimen gas from the difference in electric resistance between the sensing and temperature-compensating elements by using the heat generated by the combustion of the specimen gas on contact with a catalyst. This gas sensor also has a specimen gas intake formed in a wall of a case that contains said sensing and temperature-compensating elements and a heater to heat the specimen gas installed between the specimen gas intake and said elements.

The heater directly heats the specimen gas introduced into the gas-sensing chamber through the specimen gas intake and prevents sensitivity lowering.

BEST MODE FOR EMBODYING THE INVENTION

First Embodiment

Now details of this invention will be described by reference to the illustrated embodiments.

Figure 1:
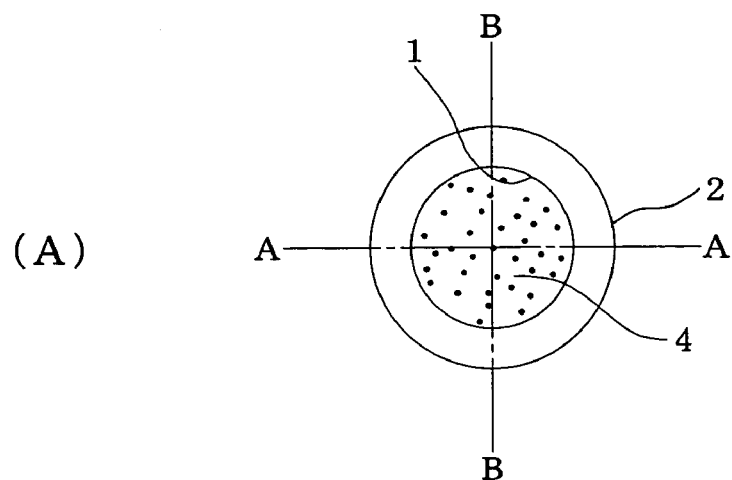
FIGS. 1(A) to (C) are top, side and bottom views showing the appearance of a first embodiment of the gas sensor according to this invention.
Figure 1:
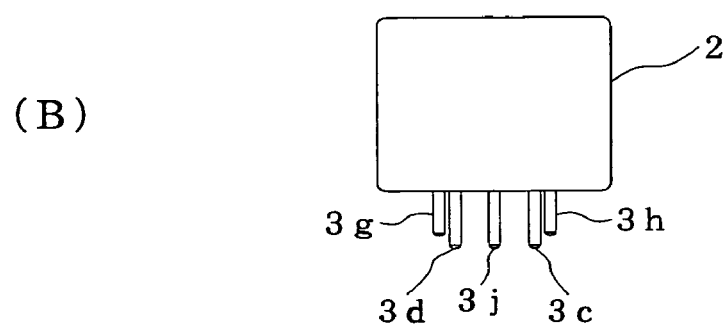
Figure 1:
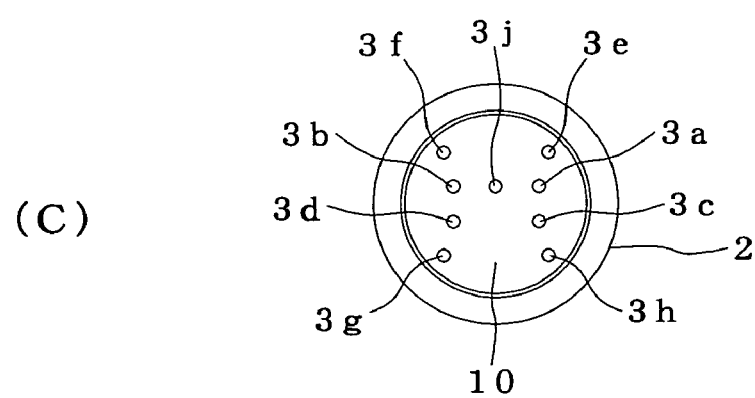
Figure 2:
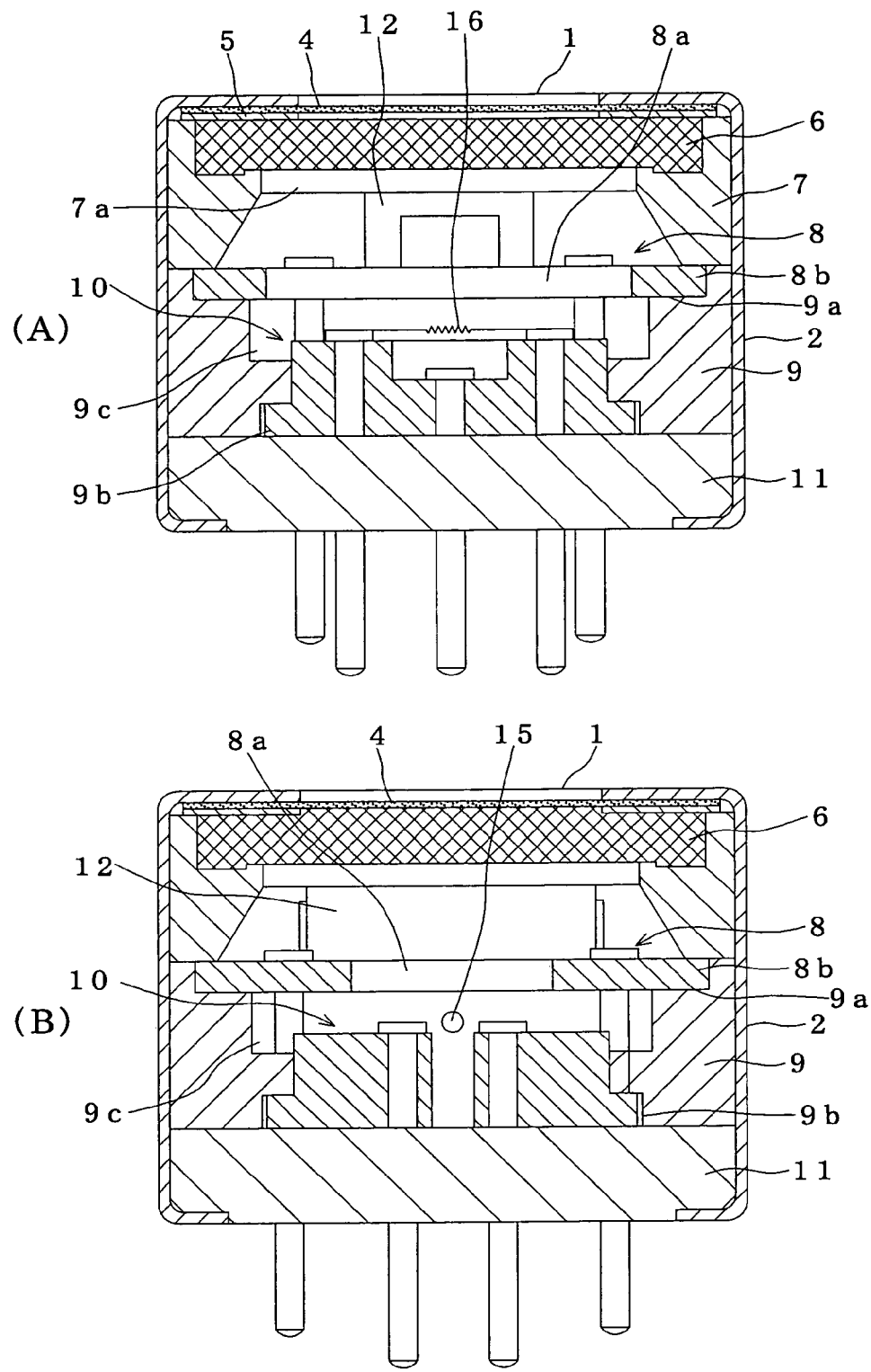
FIGS. 2(A) and (B) show cross-sectional structures taken along the lines A-A and B-B of FIG. 1.

FIGS. 1 and 2 show a first embodiment of the gas sensor according to this invention. A case 2 has a specimen gas intake 1 at one end thereof and lead pins 3a to 3h for connection at the other end thereof. The case 2 holds a water-repelling filter 4, a packing 5, a sintered porous metal sheet 6, a first spacer 7, a heating unit 8, a second spacer 9, a gas-sensing unit 10, and a base plate 11 stacked in that order from the side of the specimen gas intake 1. The other end of the case 2 is constricted and fastened so that the connection lead pins 3a to 3h and a positioning pin 3j from the gas-sensing unit 10 are pulled out.

The water-repelling filter 4 is made of a porous Teflon (registered trade mark) resin that prevents the ingress of liquid and dust. The sintered porous metal sheet 6 is made by sintering metal particles into a porous sheet.

The first spacer 7 supports the sintered porous metal sheet 6 and has a through hole 7a through which the specimen gas is passed to the heating unit 8.

Figure 3:
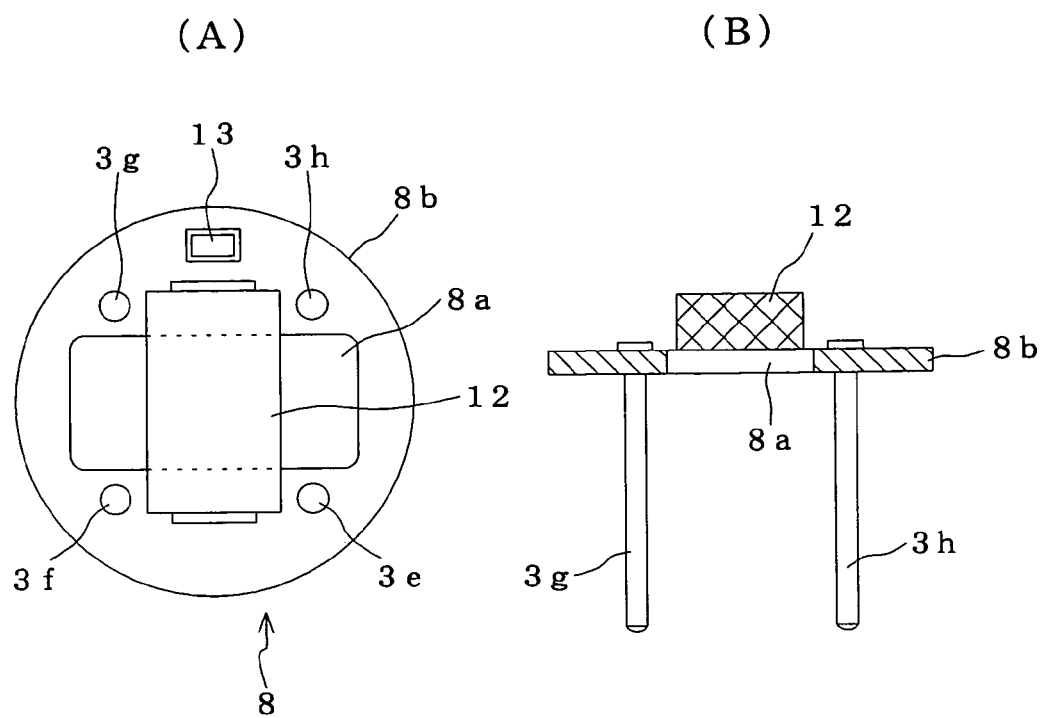
FIGS. 3(A) and (B) are front and cross-sectional views of an embodiment of a heating element constituting said gas sensor.

The heating unit 8 comprises a base plate 8b having a through hole 8a at the center thereof, with four lead pins 3e to 3h radially planted thereon, as shown in FIGS. 3(A) and (B). While a heating element 12 consisting of a chip-type resistor is mounted over the through hole 8a, a temperature-sensing element 13 is mounted on the surface of the base plate 8b. The heating and temperature-sensing elements are connected to the lead pins 3e to 3h via conductive patterns not shown.

The heater consisting of a chip-type resistor permits use of general-purpose electronic parts without necessitating special heater components, thereby providing both cost and size reduction.

The second spacer 9 has a through hole 9c through which the specimen gas passes. The through hole 9c has a top concave 9a to support the heating unit 8 and a bottom concave 9b to support the gas-sensing unit 10 at the center thereof.

Figure 4:
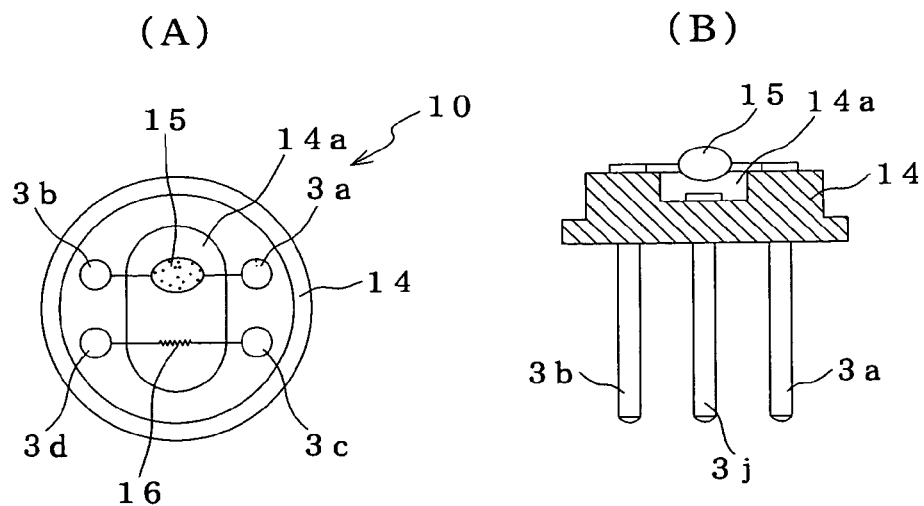
FIGS. 4(A) and (B) are front and cross-sectional views of an embodiment of a gas-sensing unit constituting said gas sensor.
Figure 5:
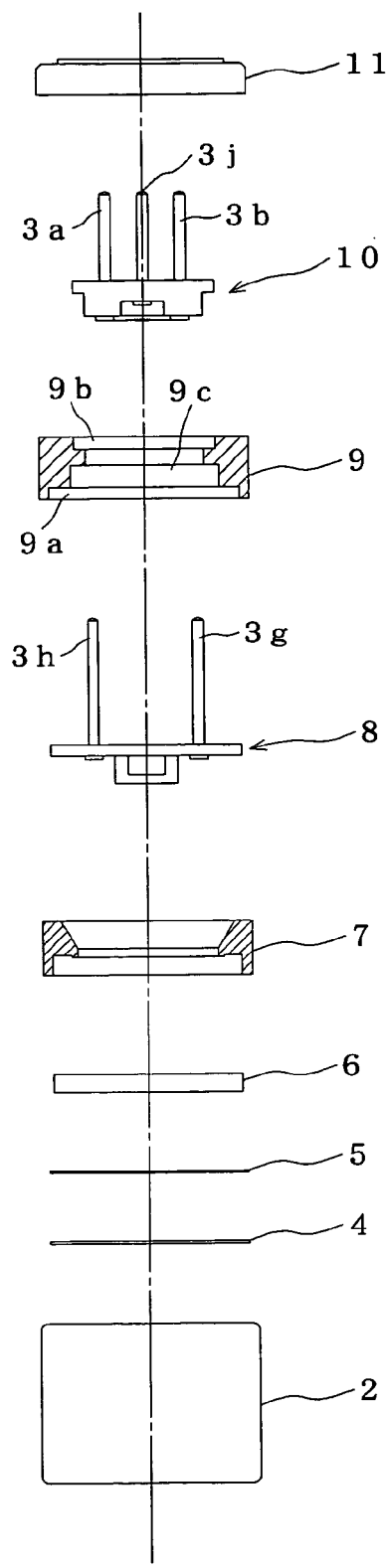
FIG. 5 shows the assembling process of said gas sensor.
Figure 6:
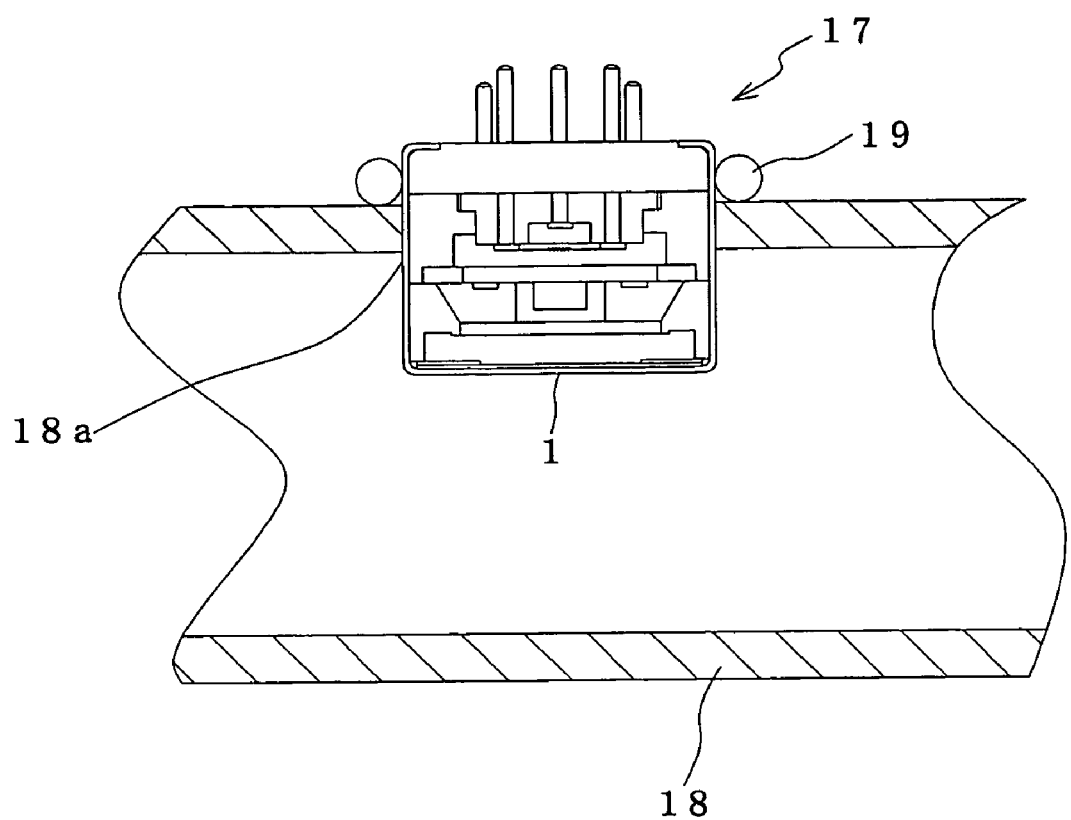
FIG. 6 is a cross-sectional view showing said gas sensor attached to a duct.

The gas-sensing unit 10 comprises a base plate 14 having a substantially elliptic through concave 14a at the center thereof, with four lead pins 3a to 3d radially planted thereon, as shown in FIGS. 4(A) and (B). A gas-sensing element 15 and a temperature-compensating element 16 are mounted over the concave 14a by connecting to lead pins 3a to 3d.

These members and units are assembled by placing the case 2 with the specimen gas intake 1 placed at the bottom, filling the water-repelling filter 4, packing 5, sintered porous metal sheet 6, first spacer 7, heating unit 8, second spacer 9 and gas-sensing unit 10, aligning the lead pins of the heating unit 8 and gas-sensing unit 10, passing the lead pins through the through hole in the base plate 11 to stack them together, and finally constricting the opening of the case 2.

Figure 16:
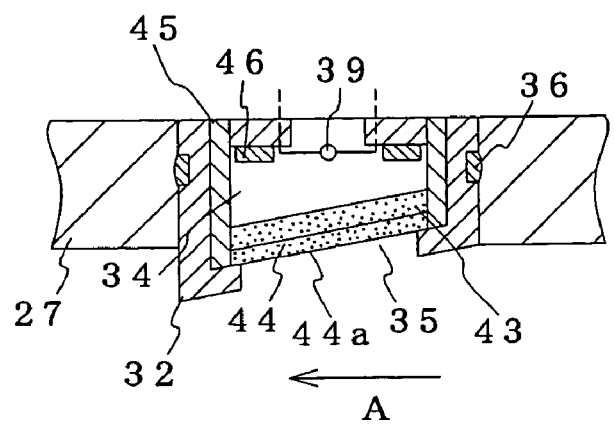
FIG. 16 is a cross-sectional view of a hydrogen sensor that is a third embodiment of the gas sensor according to this invention.

A gas sensor 17 composed as described above is fastened to a socket 18a in a duct 18 through which hot and moist fluid containing combustible gas flows via a ring-shaped packing 19 as shown in FIG. 16.

The socket 18a is preferably formed near the uppermost part of the duct 18 so that the specimen gas intake 1 of the sensor 17 points downward.

When a fluid in the atmosphere flows in through the specimen gas intake 1 in this condition, the water-repelling filter 4 removes water droplets and dusts therefrom. Then the fluid passes through the sintered porous metal sheet 6 and reaches the heating unit 8, where the fluid is heated to above the dewpoint, and then the gas-sensing unit 10. As the sintered porous metal sheet 6 is heated by the radiant heat of the heating unit 8, no condensation occurs in this area.

Based on the temperature signals from the temperature-sensing element 13, a control means not shown controls the amount of heat generated by the heating unit 8 so that the temperature optimum for the detection of the specimen gas is maintained without creating unusually high temperatures. This heat ascends by convection to raise the temperature of the atmosphere around the gas-sensing unit 10 at the uppermost top, thereby preventing the lowering the temperature around the gas-sensing element 15 and temperature-compensating element 16 and assuring the detection of the specimen gas.

The sintered porous metal sheet 6 supports the water-repelling filter 4 from behind without impairing gas permeability and prevents sudden temperature changes that might otherwise be caused by the incoming specimen gas.

While the gas-sensing unit of the embodiment described above consists of the gas-sensing element 15 and temperature-compensating element 16, the gas-sensing element alone can produce a similar effect.

While the above-described embodiment uses a chip-type resistor as the resistance element for heating, a coil of nichrome or other resistance wire can produce a similar effect.

While the spacers provide a given space to permit the use of a general-purpose gas-sensing unit in the above-described embodiment, integral concaves corresponding to said spacers formed on the base plate of the heating unit or gas-sensing unit can produce a similar effect.

Figure 7:
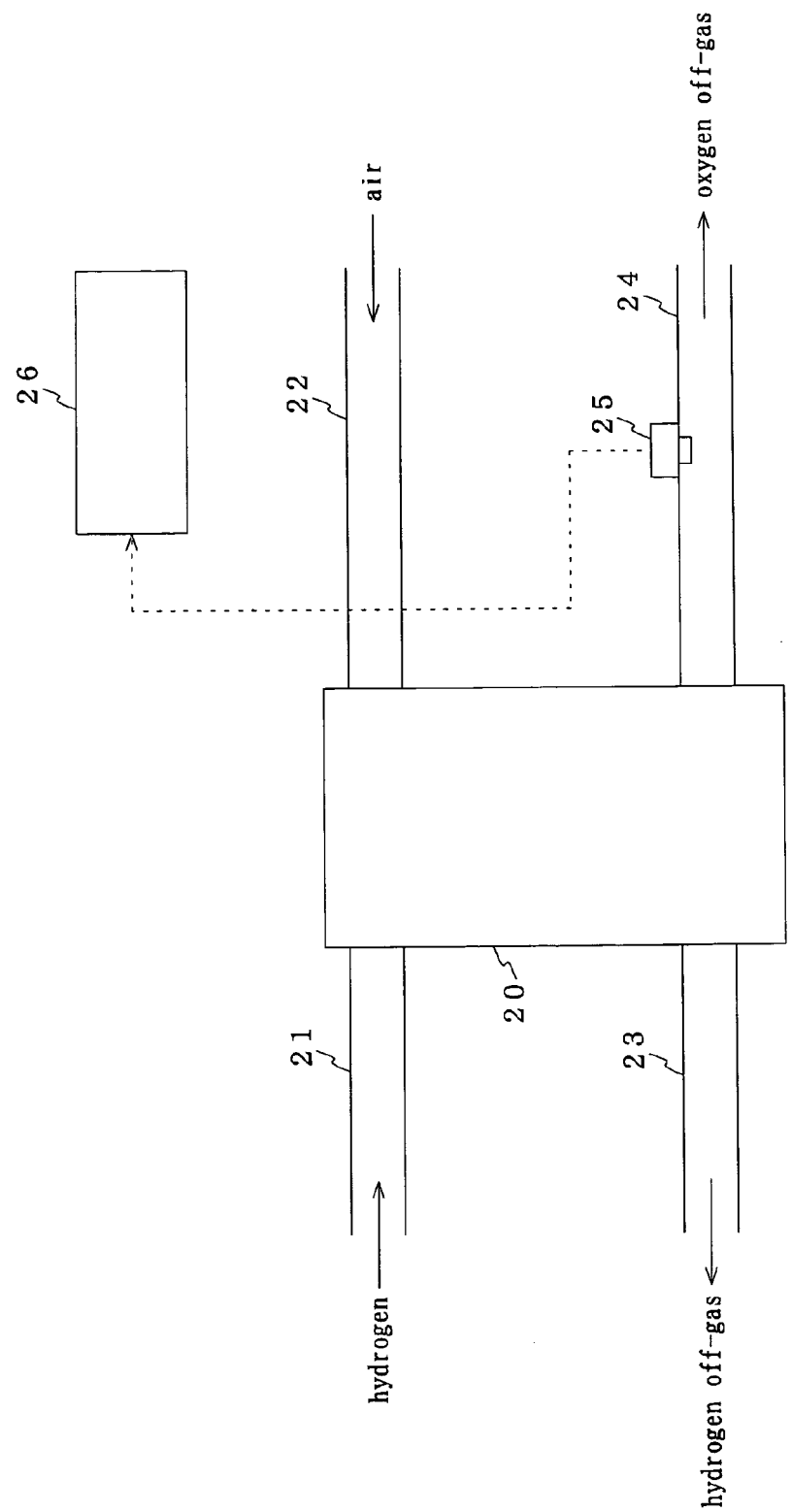
FIG. 7 is a schematic illustration of a fuel battery system to which the gas sensor of this invention is applied.

The gas sensor described above is particularly effective of the detection of combustible gases, such as hydrogen, in the exhaust pipe of the fuel battery system shown in FIG. 7.

The fuel battery 20 consists of a stack of fuel battery cells not shown each of which consists, for example, an electrolyte such as a solid polyelectrolyte membrane held between an anode-side electrode and a cathode-side electrode and also between apair of separators. Fuel gas such as hydrogen is supplied to the anode-side electrode through an entry-side passage 21, whereupon hydrogen is ionized on a catalyst electrode and moves to the cathode-side electrode via the moderately moisturized solid polyelectrolyte membrane. Electrons generated during this course of time are taken out to an external circuit for use as direct-current electric energy. As an oxidizer, such as oxygen, or air is supplied to the cathode-side electrode via an entry-side passage 22, hydrogen ions, electrons and oxygen react to form water thereat. Then, the reacted gas or off-gas is discharged to outside the system through exit passages 23 and 24 of the anode and cathode sides.

Here, a contact combustion type gas sensor that constitutes the substance of this invention (hereinafter referred to as the gas sensor) 25 is provided in the exit passage 24 on the cathode side to make it possible to ensure that no hydrogen is discharged through the exit passage 24 on the cathode side by means of a monitor 26.

Second Embodiment

Figure 8:
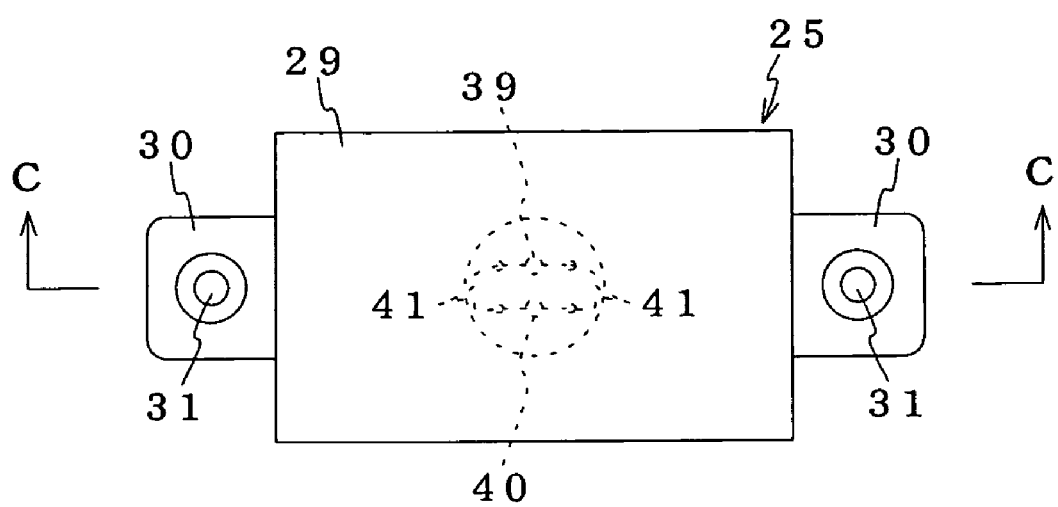
FIG. 8 is a plan view of a hydrogen sensor that is a second embodiment of the gas sensor according to this invention.
Figure 9:
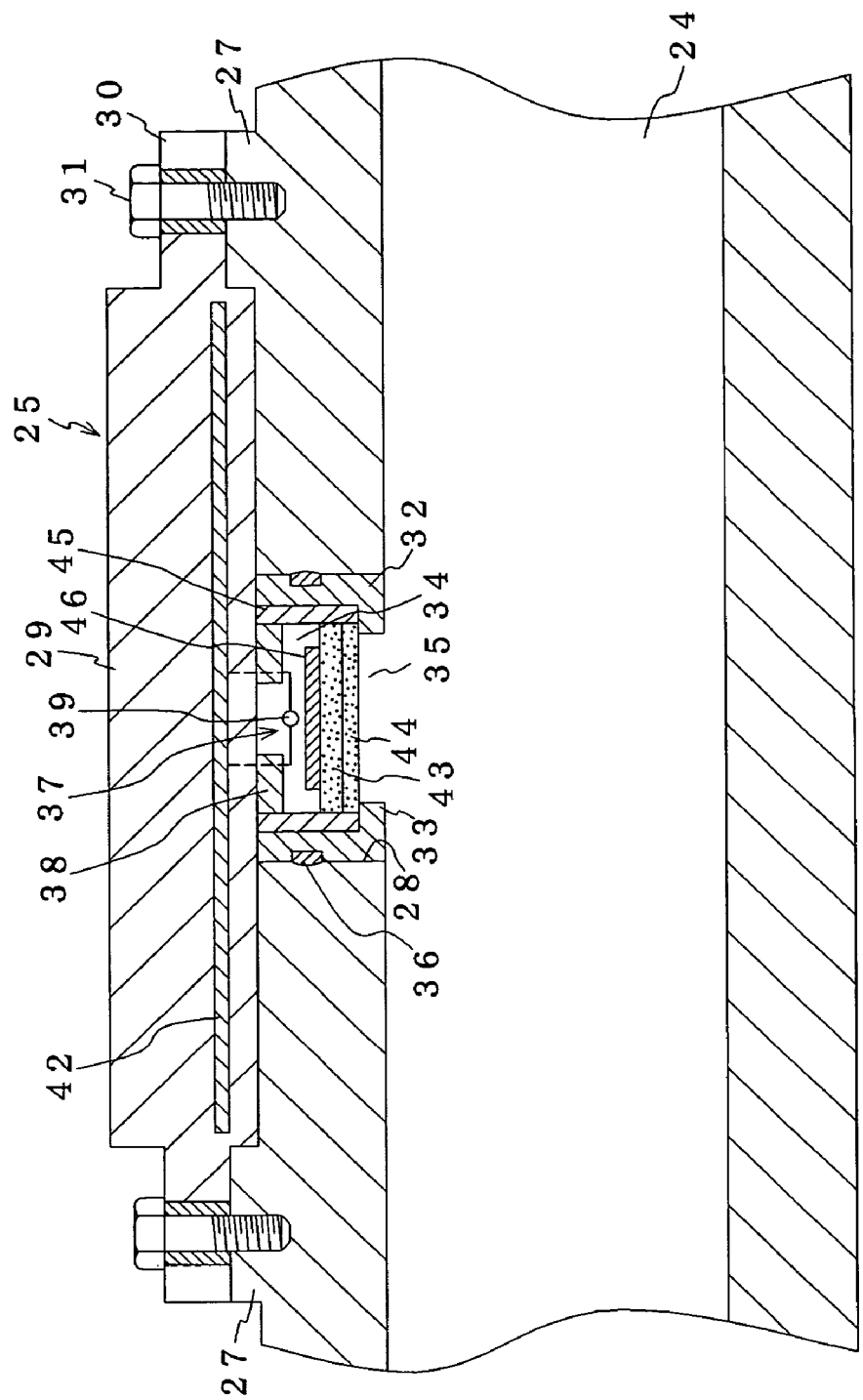
FIG. 9 is a cross-sectional view taken along the line C-C of FIG. 8.

While FIG. 8 is a plan view of a hydrogen sensor 25, FIG. 9 is a cross-sectional view taken along the line C-C of FIG. 8 showing the condition of installation of the hydrogen sensor 25.

A fitting seat 27 to fit the gas sensor 25 is provided on the exit passage 24 on the cathode side and a fitting hole 28 is provided in the peripheral wall of the exit passage 24 of the gas sensor. The gas sensor 25 has, a fitting base plate 29 of, for example, polyphenylene sulfide that has a flange 30 formed thereon. The flange 30 is fastened to the fitting seat 27 with a bolt 31. The fitting base plate 29 has a cylindrical segment 32 that is inserted in the fitting hole 28. The cylindrical segment 32 forms a case to hold the component members of the sensor, that is, a sensing element 39 and a temperature-compensating element 40.

When made of resin or other materials having a lower thermal conductivity than metals, the fitting base plate 29 provides a higher heat-insulating effect and thereby effectively prevents the dew formation on the sensor.

The cylindrical segment 32 has a gas-sensing chamber 34 on the inside thereof and a flange 33 is formed at one end of the cylindrical segment 32, that is, at the opening or a specimen gas intake 35 in the gas-sensing chamber 34. The specimen gas intake 35 is flush with the inner wall of the exit passage 24. Therefore, the gas intake 25 is perpendicular to the off-gas flowing through the exit passage 24.

A seal 36 is attached to the outer surface of the cylindrical segment 32 that sticks fast to the inner wall of the fitting hole 28. A sensor 37 is installed inside the cylindrical segment 32.

The sensor 37 has an annular base 38 of, for example, polyphenylene sulfide at the position where the other end of the cylindrical segment 32 is closed and a cylindrical metal wall 45 having the height to reach the flange 33 is provided on the outside. The paired sensing element 39 and temperature-compensating element 40 are provided at the same level through said base 38, with a required space left therebetween. A clearance is provided between the cylindrical wall 45 and cylindrical segment 32 to prevent direct heat transfer from the cylindrical metal wall 45 to the cylindrical segment 32.

Multiple sensing elements 39 may be provided for one temperature-compensating element 40.

The sensing element 39 is a contact combustion type gas sensor of known type that determines the concentration of hydrogen gas by using the electric resistance difference between the sensing element 39 at high temperature and the temperature-compensating element 40 below the ambient temperature created by the use of heat generated by the combustion of the specimen gas, that is, hydrogen that occurs when the gas comes in contact with platinum or other catalyst. The sensing element 39 and temperature-compensating element 40 are each connected and electrically connected to a circuit board 42 molded on the inside of the fitting base plate 29 via pins 41.

A sintered porous metal sheet 43 and a water-repelling filter 44 of, for example, polytetrafluoroethylene are fitted to the specimen gas intake 35 from inside the gas sensing chamber 34 in such a manner as to close the intake. The sintered porous metal sheet 43 and water-repelling filter 44 are fitted from inside said flange 33. Here, the water-repelling filter 44 blocks the passage of water droplets while permitting the passage of water vapor and the sintered porous metal sheet 43 reinforces the water-repelling filter 44 without increasing air flow resistance.

Figure 10:
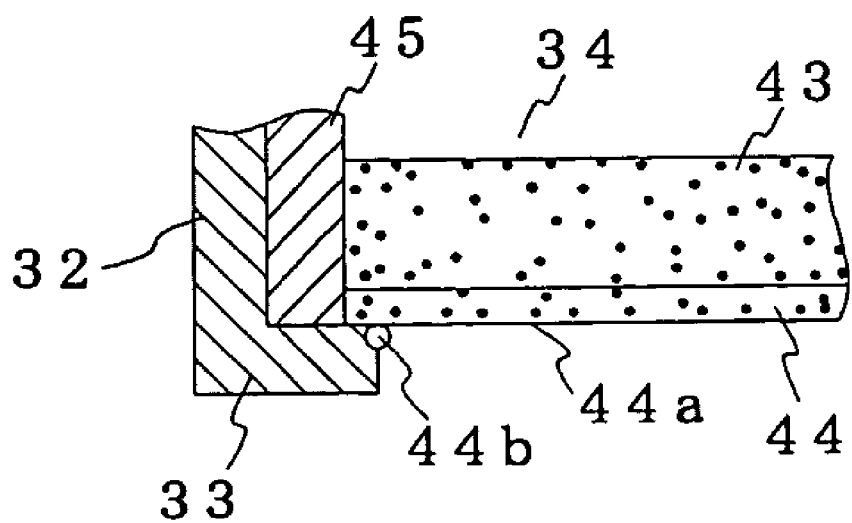
FIG. 10 is an enlarged cross-sectional view of a part to which a water-repelling filter is attached.

As the part of the outer surface 44a of the water-repelling filter 44 is welded to the inner edge of the flange 33 to form a weld 44b throughout the entire perimeter thereof as shown in FIG. 10, no water enters inside through between the flange 33 and water-repelling filter 44.

A heater 46 to heat the specimen gas is provided in the gas-sensing chamber 34 described above.

Figure 11:
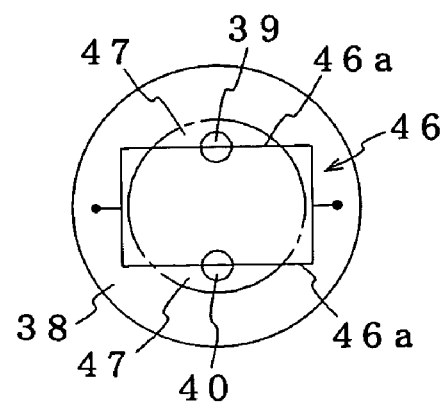
FIGS. 11(A) and (B) are schematic and elemental perspective views showing the relationship between the position of the heater and the base of the second embodiment.
Figure 11:
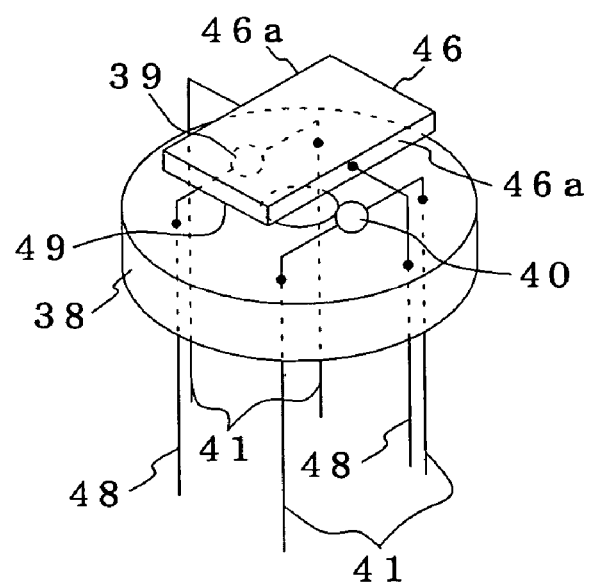

While FIG. 11(A) is a schematic view showing the positional relationship between the heater 46 and base 38, FIG. 11(B) is a perspective view showing the principal part thereof.

As shown in FIGS. 11(A) and (B), the heater 46 is a four-sided plate member, with the sensing element 39 and temperature-compensating element 40 disposed on the longer sides 46a thereof., and placed in such a manner as to block the specimen gas intake 35. The heater 46 is large enough to provide a semicircular gas lead-in segment 47 between each longer side 46a and the inner periphery of the specimen gas intake 35, as indicated by the chain line in FIG. 11(A). The heater 46 has a heat-release surface 49 that faces the gas-sensing chamber 34 and is located equal distance from the sensing element 39 and temperature-compensating element 40.

As the sensing element 39 and temperature-compensating element 40 thus abut each gas lead-in segment 47, the heater 46 divides the specimen gas flowing in through the specimen gas intake 35 into the semicircular gas lead-in segments 47. After passing through the sensing element 39 and temperature-compensating element 40, the specimen gas then enters the gas-sensing chamber 34. The leadwire 48 of the heater 46 is connected to the circuit board 42 (the same applies in the embodiments to be described hereunder).

In the embodiment just described, the heater 46 directly heats the specimen gas in the gas-sensing chamber 34. Also, the water-repelling filter 44 prevents the ingress of condensed water through the specimen gas intake 35. The specimen gas having passed the sintered porous metal sheet 43 is directly heated by the heat-release surface 49 after passing the heater 46. As the relative humidity of the specimen gas or off-gas thus drops, condensation of moisture in the off-gas in the gas-sensing chamber is surely prevented. This eliminates the adherence of condensed water to the sensing element 39 that could cause element breakdown and sensitivity lowering and, thus, prolongs the life of the sensing element 39.

In particular, the specimen gas admitted through the specimen gas intake 35 into the gas-sensing chamber 34 is, after being heated by the heater 46 and passing through the inlets 47, is evenly divided between the sensing element 39 and temperature-compensating element 40 in the gas-sensing chamber 34. Accordingly, the sensing element 39 and temperature-compensating element 40 are exposed to the specimen gas under the same conditions. This evenly brings the sensing element 39 and temperature-compensating element 40 into contact with the specimen gas and, thereby, assures the determination of the concentration of the specimen gas with high accuracy. Also, uniform heating of the sensing element 39 and temperature-compensating element 40 by the heater 46 assures high-accuracy sensing.

Second Embodiment of the Heater

Figure 12:
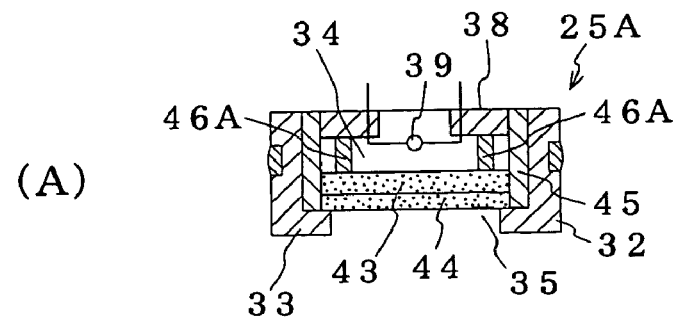
FIGS. 12(A) to (C) are a cross-sectional view of a third embodiment and schematic and elemental perspective views showing the relationship between the heater and the base thereof.
Figure 12:
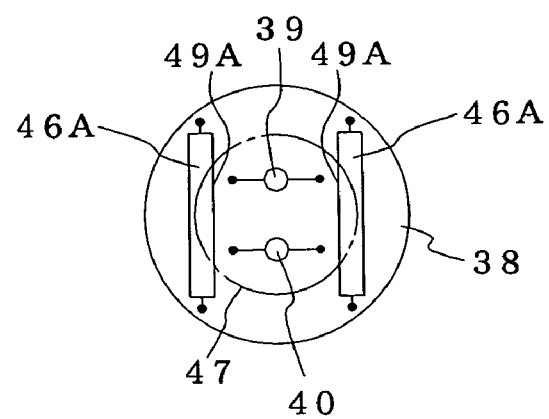
Figure 12:
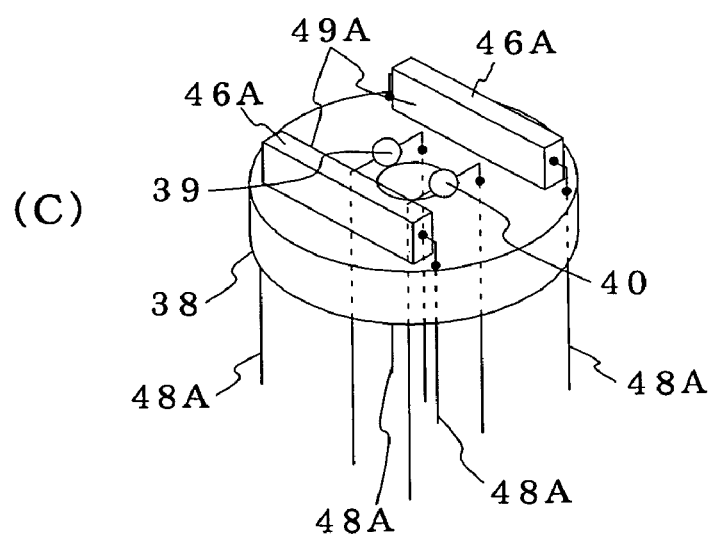

A gas sensor 25A shown in FIGS. 12(A) to (C) is the same with the above-described one in the basic configuration. One common point is that the gas sensor 25A is fitted to the fitting seat 27 in the exit passage 24 on the cathode side by means of the flange 30 and the cylindrical segment 32 is inserted in the fitting hole 28. Another common point is that the inside of the cylindrical segment 32 constitutes the gas-sensing chamber 34, the flange 33 is formed at one end thereof, and the inside of the flange 33 constitutes the specimen gas intake 35. And a third common point is that the annular base 38 is provided at the position where the other end of the cylindrical segment 32 is closed, a cylindrical metal wall 45 having the height to reach the flange 33 is provided on the outside, and the paired sensing element 39 and temperature-compensating element 40 are provided through said base 38.

In the gas-sensing chamber 34, paired heaters 46A, 46A each having a heat-release surface 49A extending along the direction in which the specimen gas flows in or, in other words, in which the specimen gas intake 35 lies are disposed between the base 38 and sintered porous metal sheet 43. Said sensing element 39 and temperature-compensating element 40 are disposed between said heaters 46A, 46A. The paired heaters are disposed with the heat-release surfaces 49A facing each other and said sensing element 39 and temperature-compensating element 40 are disposed therebetween, with each of said elements being positioned at equal distance from the heat-release surface 49A of each heater 46A. Reference numeral 48A denotes the leadwire of the heater 46A.

In this embodiment, the water-repelling filter 44 blocks the ingress of condensed water and the specimen gas having passed the sintered porous metal sheet 43 is smoothly admitted into the gas-sensing chamber 34 without being obstructed by other members and directly heated from both sides by the heat-release surfaces 49A of the paired heaters 46A. As the relative humidity of the specimen gas or off-gas thus drops, condensation of moisture in the off-gas in the gas-sensing chamber is surely prevented. This eliminates the adherence of condensed water to the sensing element 39 that could cause element breakdown and sensitivity lowering and, thus, prolongs the life of the sensing element 39.

A particular advantage of this embodiment is that the heaters 46A do not block the admittance of the specimen gas. Being positioned, in addition, at equal distance from the heat-release surface 49A of each heater 46A, the sensing element 39 and temperature-compensating element 40 are uniformly heated and, therefore, assure gas sensing with high accuracy. Furthermore, the heaters 46A functioning as spacers to keep desired space between the sintered porous metal sheet 43 and water-repelling filter 44 and the base 38 increases the reliability in fitting the sintered porous metal sheet 43 and water-repelling filter 44. The greater heat-release surface 49A secured in a space defined by the heaters 46A, 46A enhances the heating capacity and contributes to power conservation. The heaters 46A that can be mounted on the base 38 together with the sensing element 39 and temperature-compensating element 40 provide an advantage in assembling.

Third Embodiment of the Heater

Figure 13:
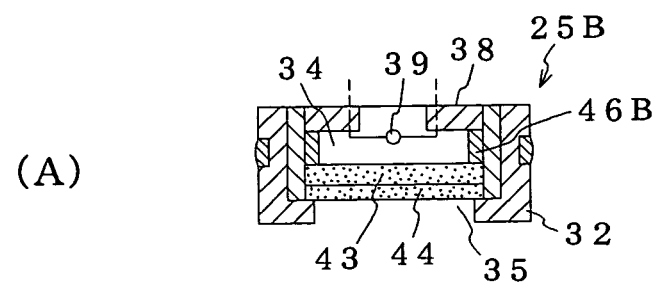
FIGS. 13(A) to (C) are a cross-sectional view of a fourth embodiment and schematic and elemental perspective views showing the relationship between the heater and the base thereof.
Figure 13:
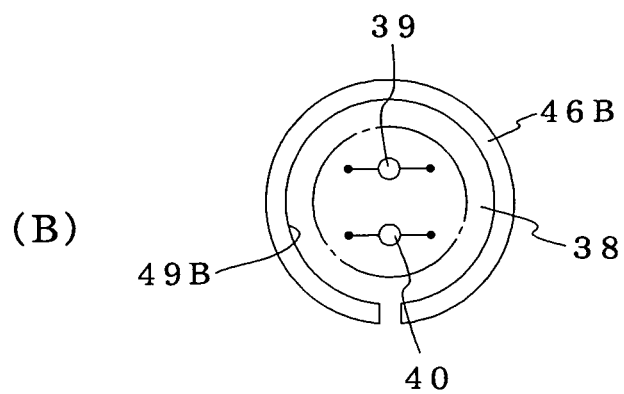
Figure 13:
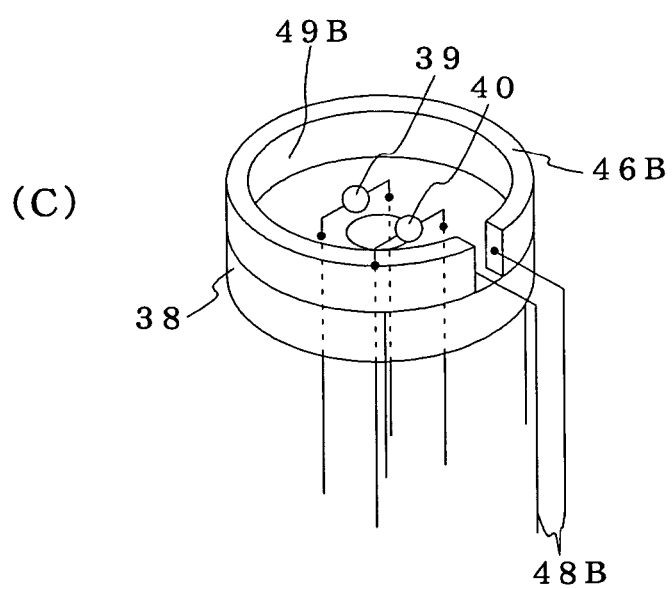

A gas sensor 25B shown in FIGS. 13(A) to (C) has a cylindrical heater 46B in place of the paired heaters 46A in the second embodiment described above. The heater 46B has a substantially C-shaped cross-section, with the axis of the cylindrical shape disposed along the direction in which the specimen gas flows in. Therefore, the heater 46B surrounds the sensing element 39 and temperature-compensating element 40. To be more specific, the heater 46B is disposed so as to lie along the outer periphery of the base 38 and extends from the base 38 to the sintered porous metal sheet 43. Reference numeral 48B designates the leadwire of the heater 46B.

As such, this embodiment also prolongs the life of the sensing element 39 by directly heating the specimen gas in the gas-sensing chamber 34 with the heater 46B. Having a greater heat-release surface 49B covering the entire periphery than the heater 46A of the third embodiment shown in FIG. 12, the heater 46B heats the entirety of the gas-sensing chamber evenly and uniformly, thereby assuring the determination of gas concentration with higher accuracy. Furthermore, the cylindrical heater 46B provides a greater heat-release surface in a limited space and, therefore, assures efficient heating of the specimen gas in the gas-sensing chamber, which, in turn, is conducive to power conservation.

Having a cylindrical shape lying along the direction in which the specimen gas flows in, the heater 46B of this embodiment also permits smooth admittance of the specimen gas without offering any hindrance. Also, the heater 46B functioning as a spacer to keep desired space between the sintered porous metal sheet 43 and water-repelling filter 44 and the base 38 increases the reliability in fitting the sintered porous metal sheet 43 and water-repelling filter 44 and, at the same time, enhances the rigidity of the heater 46B itself. The heater 46B that can be mounted on the base 38 together with the sensing element 39 and temperature-compensating element 40 provides an advantage in assembling.

Fourth Embodiment of the Heater

Figure 14:
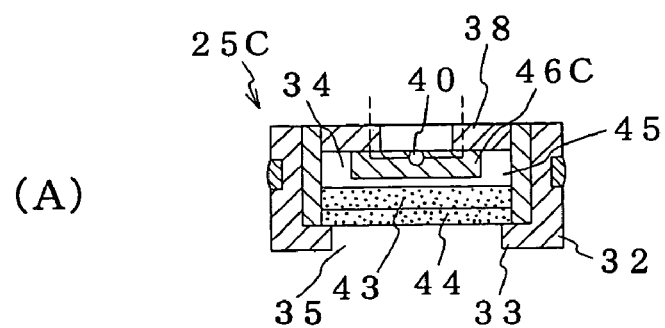
FIGS. 14(A) to (C) are a cross-sectional view of a fifth embodiment and schematic and elemental perspective views showing the relationship between the heater and the base thereof.
Figure 14:
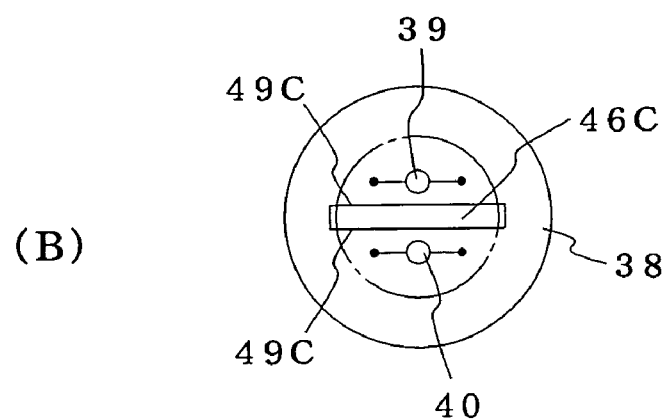
Figure 14:
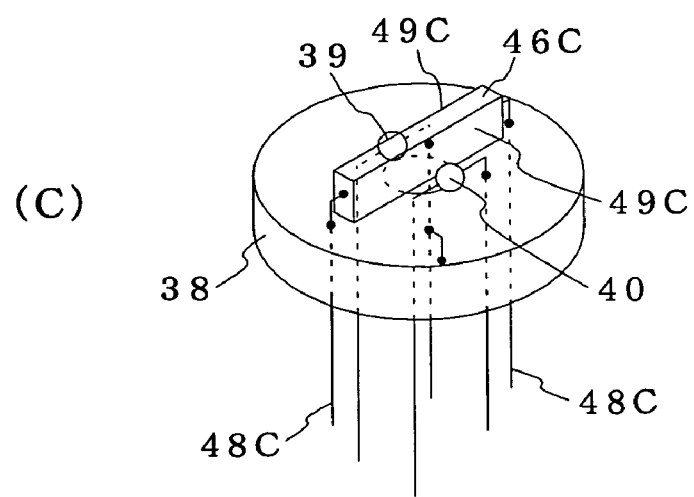

A gas sensor 25C shown in FIGS. 14(A) to (C) is the same with the above-described ones in the basic configuration. One common point is that the gas sensor 25C is fitted to the fitting seat 27 in the exit passage 24 on the cathode side by means of the flange 30 and the cylindrical segment 32 is inserted in the fitting hole 28. Another common point is that the inside of the cylindrical segment 32 constitutes the gas-sensing chamber 34, the flange 33 is formed at one end thereof, and the inside of the flange 33 constitutes the specimen gas intake 35. And a third common point is that the annular base 38 is provided at the position where the other end of the cylindrical segment 32 is closed, a cylindrical metal wall 45 having the height to reach the flange 33 is provided on the outside, and the paired sensing element 39 and temperature-compensating element 40 are provided through said base 38.

In this embodiment, a tabular heater 46C lying along the direction in which the specimen gas flows in is disposed between the sensing element 39 and temperature-compensating element 40. The tabular heater 46C is disposed with the heat-release surfaces 49C thereof faced toward the sensing element 39 and temperature-compensating element 40. That is, the vertical surfaces shown in the figure are the heat-release surfaces 49C of the heater 46C. Reference numeral 48C designates the leadwire of the heater 46C.

In this embodiment, the specimen gas entering the specimen gas intake 35 is led, after passing through the water-repelling filter 44 and sintered porous metal sheet 43, along the heater 46C to the gas-sensing chamber 34 and then directly heated by the heat-release surfaces 49C. The specimen gas thus heated in turn heats the sensing element 39 and temperature-compensating element 40. This embodiment also prolongs the life of the sensing element 39 by heating the inside of the gas-sensing chamber 34 with the heater 46C basically in the same manner as the above-described embodiments. In particular, the sensing element 39 and temperature-compensating element 40 exposed to the specimen gas under the same conditions and evenly heated by the heater 46C assures high-accuracy determination of the concentration of the specimen gas. The heater 46C that can be mounted on the base 38 together with the sensing element 39 and temperature-compensating element 40 provides an advantage in assembling.

Fifth Embodiment of the Heater

Figure 15:
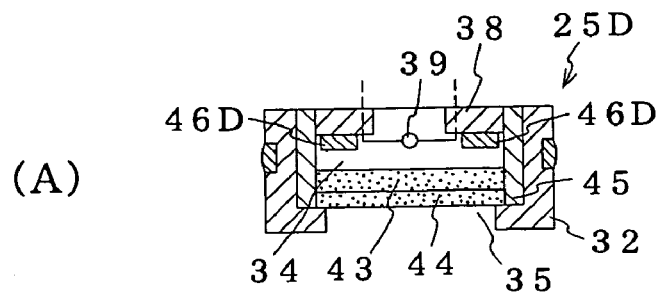
FIGS. 15(A) to (C) are a cross-sectional view of a sixth embodiment and schematic and elemental perspective views showing the relationship between the heater and the base thereof.
Figure 15:
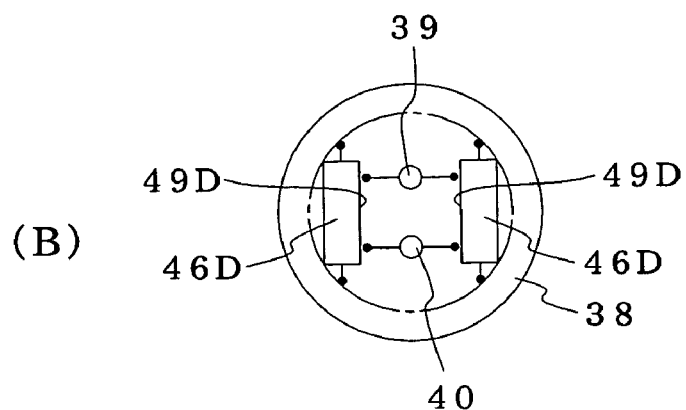
Figure 15:
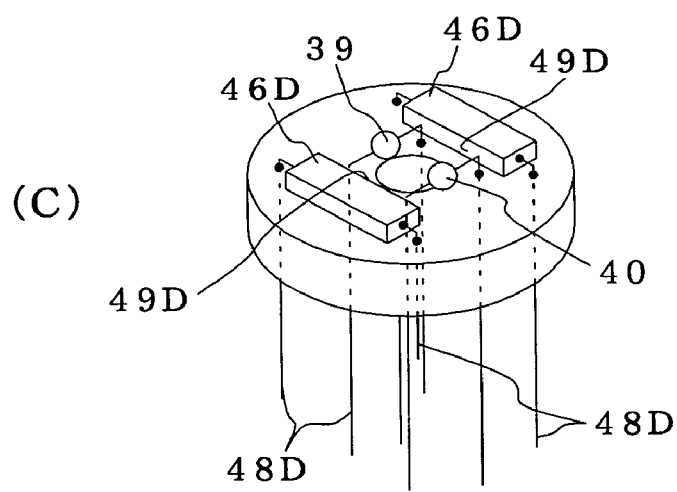

In the embodiment shown in FIGS. 15(A) to (C), paired heaters 46D lying along the surface of the base 38 are disposed on the outside of the sensing element 39 and temperature-compensating element 40. That is, the sensing element 39 and temperature-compensating element 40 are disposed between the paired heaters 46D at equal distance there from. The two rectangular heaters 46D, with the heat-release surfaces 49D thereof facing toward the specimen gas intake 35, heat the gas-sensing chamber 34. Reference numeral 48D denotes the leadwire of the heater 46D.

This embodiment also prolongs the life of the sensing element 39 by directly heating the inside of the gas-sensing chamber 34 with the heaters 46D in the same manner as the above-described embodiments. In particular, the heaters 46D that can be mounted on the base together with the sensing element 39 and temperature-compensating element 40 facilitate the supporting of the heaters 46D and manufacturing of the same.

Description of the Structure of the Specimen Gas Intake

To the specimen gas intake 35 are fitted the sintered porous metal sheet 43 and the water-repelling filter 44 of, for example, polytetrafluoroethylene from within the gas-sensing chamber 34 in such a manner as to close the intake. The sintered porous metal sheet 43 and water-repelling filter 44 are fitted from within the flange 33. The water-repelling filter 44 having a thickness of 150 µm to 300 µm blocks the passage of water droplets while permitting the passage of water vapor.

When the thickness is less than 150 µm, the water-repelling filter 44 might be damaged by the projections of metal particles constituting the sintered porous metal sheet 43. When the thickness is more than 300 µm, the water-repelling filter 44 might increase resistance to gas flow, thereby lowering the response and sensitivity to the specimen gas.

The hydrogen sensor 25 described above can determine the concentration of the hydrogen in the off-gas as the off-gas flowing through the exit passage 24 is admitted into the gas-sensing chamber 34 through the specimen gas intake 35, sintered porous metal sheet 43 and water-repelling filter 44.

As the water in the off-gas is prevented from entering the gas-sensing chamber 34 by the water-repelling filter 44, the gas-sensing element 39 and temperature-compensating element 40 are kept from wetting. This prevents the element breakdown and sensitivity lowering of the hydrogen sensor 25 and prolongs the life thereof. In addition, provision of the water-repelling filter 44 on the outer side of the sintered porous metal sheet 43 prevents the clogging of the sintered porous metal sheet 43 with water.

Second Embodiment of the Specimen Gas Intake

In a hydrogen sensor 25 shown in FIG. 16, the sintered porous metal sheet 43 and the water-repelling filter 44 of, for example, polytetrafluoroethylene are fitted to the specimen gas intake 35 from within the gas-sensing chamber 34 in such a manner as to close the intake. The sintered porous metal sheet 43 and water-repelling filter 44 are fitted from within the flange 33. The water-repelling filter 44 having a thickness of 150 µm to 300 µm blocks the passage of water droplets while permitting the passage of water vapor.

This embodiment is characterized in that the specimen gas intake 35 protrudes to the inside of the exit passage 24. That is, the cylindrical segment 32 and cylindrical wall 45 are formed so that the specimen gas intake 35 inclines downward toward the downstream of the flow (indicated by the arrow A) of the off-gas in the exit passage 24.

The sintered porous metal sheet 43 and water-repelling filter 44 fitted to the specimen gas intake 35 in such a manner as to close the intake also incline downward toward the downstream of the flow of the off-gas. The direction of the off-gas flow is the same as that of hydrogen gas when the off-gas contains the hydrogen gas to be sensed.

The hydrogen sensor 25 just described prevents the ingress of water into the gas-sensing chamber 34 and keeps the gas-sensing element 39 from wetting. Even if the water contained in the off-gas adheres to the outer surface 44a of the water-repelling filter 44, the adhered water flows downward along the outer surface 44a and is blown away by the stream of the off-gas. Therefore, no water remains on the outer surface 44a of the water-repelling filter 44. As a consequence, the outer surface 44a of the water-repelling filter 44 remains unclogged by the liquid and allows the continuation of the gas flow. This assures the uninterrupted flow of the gas into the gas-sensing chamber 34 and continuous sensing of the hydrogen gas contained in the off-gas.

Third Embodiment of the Specimen Gas Intake

Figure 17:
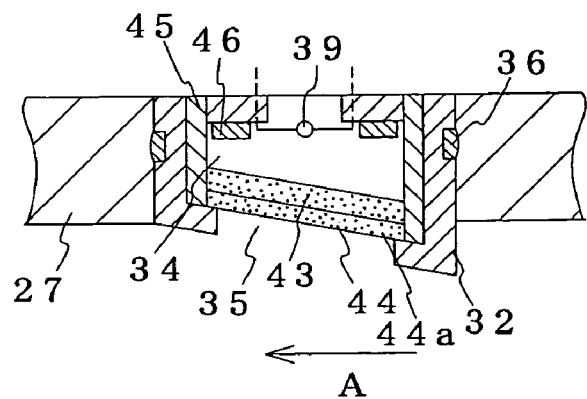
FIG. 17 is a cross-sectional view of a hydrogen sensor that is a fourth embodiment of the gas sensor according to this invention.

In a hydrogen sensor 25 shown in FIG. 17, the specimen gas intake 35 protrudes to the inside of the exit passage 24. That is, the cylindrical segment 32 and cylindrical wall 45 are formed so that the specimen gas intake 35 inclines upward to the downstream of the flow (indicated by the arrow A) of the off-gas in the exit passage 24. The sintered porous metal sheet 43 and water-repelling filter 44 fitted to the specimen gas intake 35 in such a manner as to close the intake also incline upward to the downstream of the off-gas flow. The direction of the flow of the off-gas is the same as that of hydrogen gas when the off-gas contains the hydrogen gas to be sensed.

The hydrogen sensor 25 just described prevents the ingress of water into the gas-sensing chamber 34 and keeps the gas-sensing element 39 from wetting. As, in addition, the upstream half of the off-gas flow functions as a shield, the water contained in the off-gas does not come in direct contact with the water-repelling filter 44 and, therefore, is prevented from adhering to the outer surface 44a of the water-repelling filter 44. As a consequence, the outer surface 44a of the water-repelling filter 44 remains unclogged by the liquid and allows the continuation of the gas flow. This assures the uninterrupted flow of the gas into the gas-sensing chamber 34 and continuous sensing of the hydrogen gas contained in the off-gas. The cylindrical segment 32 functioning as the shield suppresses the influence of the gas flow rate on the sensing accuracy of the hydrogen sensor 25.

Fourth Embodiment of the Specimen Gas Intake

Figure 18:
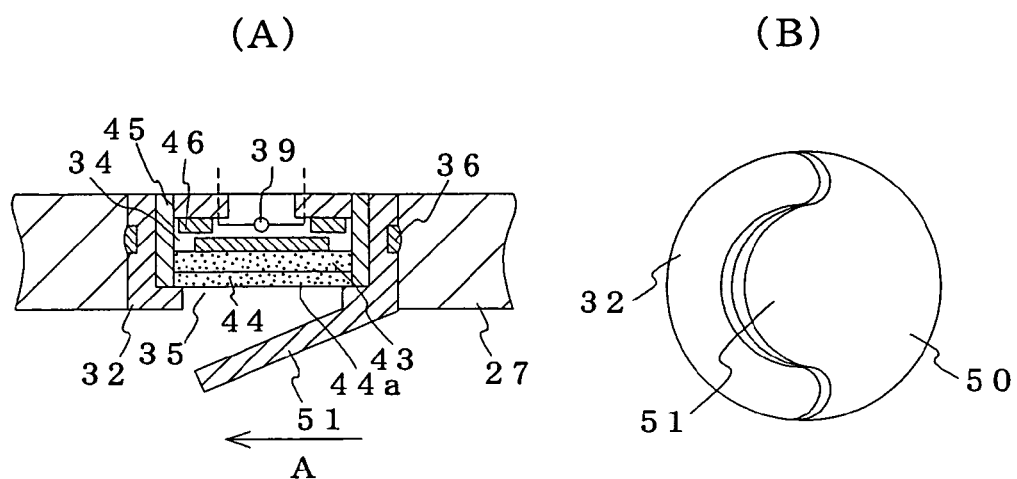
FIGS. 18(A) and (B) are cross-sectional and elemental bottom views of a hydrogen sensor that is a fifth embodiment of the gas sensor according to this invention.

The embodiment shown in FIG. 18 has a water-ingress preventing cover 50 at an end of the exit passage 24 in the cylindrical segment. The water-ingress preventing cover 50 protrudes from the substantially semicircular portion of the edge of the cylindrical segment 32 on the upstream side of the off-gas flow (indicated by the arrow A) and has tongue 51 extending obliquely downward toward the downstream side. The tongue 51 is away from the substantially semicircular portion of the edge of the cylindrical segment 32 on the downstream side of the off-gas flow. As shown in FIG. 18(B), the tongue 51 is provided in such a manner as to substantially cover the specimen gas intake 35 when viewed in a plan view. As such, the tongue 51 is apart from the water-repelling filter 44.

The hydrogen sensor 25 just described prevents the ingress of water into the gas-sensing chamber 34 and keeps the gas-sensing element 39 from wetting. In addition, the water-ingress preventing cover 50 blocks the water contained in the off-gas and keeps the water from reaching the specimen gas intake 35. Therefore, the water contained in the off-gas does not come in direct contact with the water-repelling filter 44 and, therefore, is prevented from adhering to the outer surface 44a of the water-repelling filter 44. As a consequence, the outer surface 44a of the water-repelling filter 44 remains unclogged by the liquid and allows the continuation of the gas flow. This assures the uninterrupted flow of the gas into the gas-sensing chamber 34 and continuous sensing of the hydrogen gas contained in the off-gas. The water-ingress preventing cover 50 functioning as the shield suppresses the influence of the gas flow rate variations on the sensing accuracy of the hydrogen sensor 25.

Embodiment of the Fluid-tight Structure of the Flange and Water-repelling Filter In the embodiments described above, water joins the outer surface 44a of the water-repelling filter 44 with the inner periphery of the flange 33 so as to prevent the ingress of water through therebetween. This water can be replaced by the structures shown in FIGS. 19(A) and (B) and FIG. 20. Each structure will be described by reference to the relevant drawing.

Figure 19:
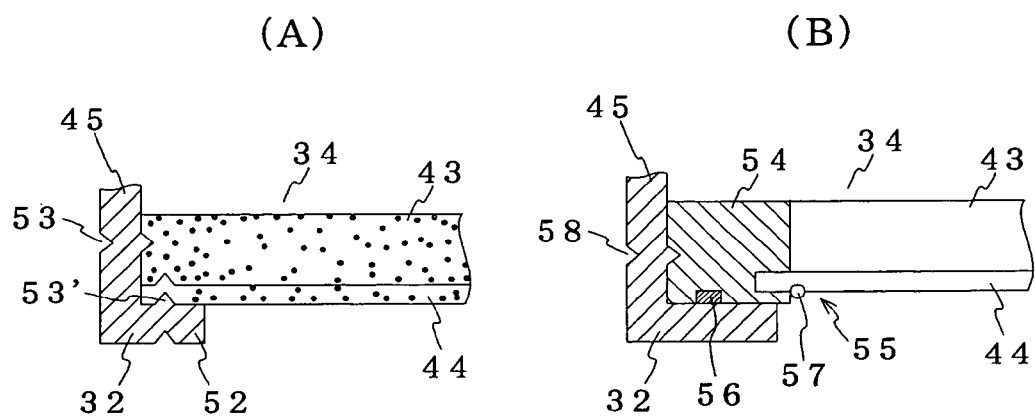
FIGS. 19(A) and (B) are enlarged cross-sectional views showing another example of the structure of the part to which the water-repelling filter is attached.

The embodiment shown in FIG. 19(A) has an inwardly protruding flange 52 at the inner end of the exit passage 24 in the cylindrical metal wall 45. The sintered porous metal sheet 43 and water-repelling filter 44 are fitted on the gas-sensing chamber side of the flange 52. The cylindrical metal wall 45 and sintered porous metal wall 43 are tightly joined by forming a projection 53 by annually crimping the outer periphery of the cylindrical metal wall 45. Also, the flange 52 and water-repelling filter 44 are tightly joined by forming a projection 53' by annually crimping the flange 52, thereby preventing the ingress of water.

The embodiment shown in FIG. 19(B) prepares a water-repelling filter unit 55 comprising an annular resin filter ring 54 attached to the outer periphery of the water-repelling filter 44 whose outer surface 44a is welded to the entire inner periphery of the filter ring 54. The water-repelling filter 44 and sintered porous metal sheet 43 are stacked together and placed inside the cylindrical metal wall 45, with a seal 56 filled between the filter ring 54 and the flange 52 of the cylindrical metal wall 45. In addition, the outer periphery of the cylindrical metal wall 45 is annually crimped to tightly join the cylindrical metal wall 45 and filter ring 54, thereby preventing the ingress of water. In FIG. 19(B), reference numerals 57 and 58 designate a weld and a crimp, respectively.

Figure 20:
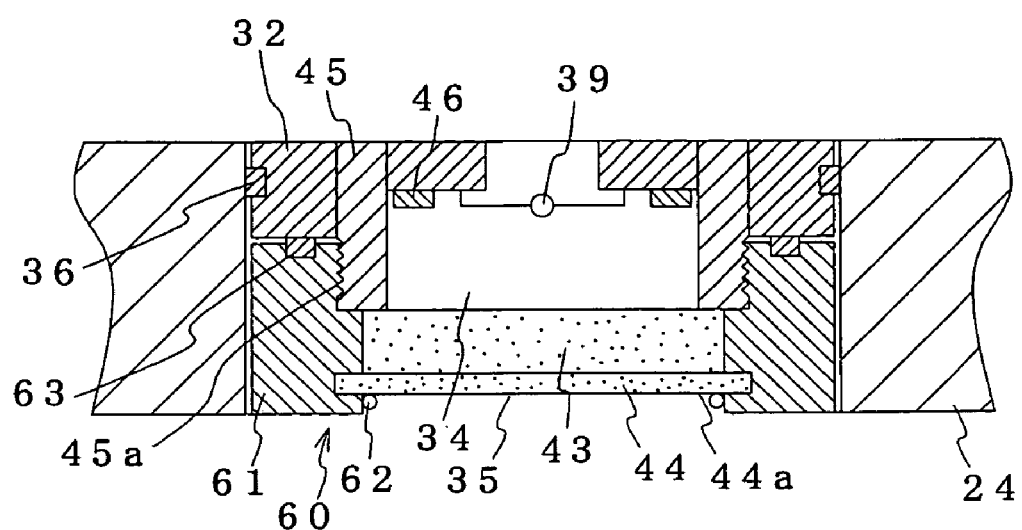
FIG. 20 is an enlarged cross-sectional view showing still another example of the structure of the part to which the water-repelling filter is attached.

FIG. 20 shows an embodiment comprising a replaceable cap 60 in which the sintered porous metal sheet 43 and water-repelling filter 44 are assembled as a unit that is screwed on to the cylindrical metal wall 45.

To be more specific, the cylindrical segment 32 is shorter than the cylindrical metal wall 45. The portion of the cylindrical metal wall 45 protruding from the cylindrical segment 32 forms a threaded portion 45a. The cap 60 comprises the water-repelling filter 44 fitted to a cylindrical resin cap proper 61, with the outer surface 44a of the water-repelling filter 44 welded to the entire inner periphery of the cap proper 61 and the sintered porous metal sheet 43 fitted on the inside of the water-repelling filter 44 in the cap proper 61. The inner edge of the cap proper 61 on the outside of the water-repelling filter 44 constitutes the specimen gas intake 35. In FIG. 20, reference numeral 62 denotes the weld.

The cap 60 is screwed on to the threaded portion 45a and a seal 63 is filled between the cap proper 61 and cylindrical segment 32 to keep gas-tightness therebetween. When the hydrogen sensor 25 is fitted in the exit passage 24, a seal 36 is provided between the outer surface of the cylindrical segment 32 and the inner wall of the exit passage 24 to keep gas-tightness therebetween. This cap 60 is easy to mount and dismount and, therefore, facilitates the replacement of the sintered porous metal sheet 43 and water-repelling filter 44.

OTHER EMBODIMENTS

This invention is not limited to the embodiments described above.

For example, the specimen gas is not limited to hydrogen gas but may be other gases. The gas sensor is not limited to the hydrogen sensor but may be adapted to sense other gases. Furthermore, the gas sensor is not limited to the hydrogen sensor that determines the concentration of hydrogen in the off gas from the cathode of fuel batteries.

The gas sensor is not limited to the contact combustion type gas sensor but may also serve as metal oxide semiconductor, gas thermal conductivity, infrared transmission, reflection and electrochemical gas sensors.

INDUSTRIAL APPLICABILITY

This invention prevents the lowering of sensitivity and breakdown of elements by preventing the wetting of elements and occurrence of water condensation in the gas-sensing chamber by preventing the water contained in the gas flowing in the passage from entering the gas-sensing chamber. This invention thus permits sure sensing of hot and moist specimen gas flowing through the exit passage on the cathode side of solid polymer membrane type and other types of fuel batteries.

What is claimed is:

1. A gas sensor comprising:
a gas-sensing element comprising a catalyst;
a temperature-compensating element;
a case holding said elements;
a chip-type resistor heater disposed between a specimen gas intake of the case and the gas-sensing and temperature-compensating elements; and
a water-repelling filter disposed at the specimen gas intake of the case; wherein the concentration of a specimen gas is determined from the difference in electrical resistance between the gas-sensing element and the temperature-compensating element.

2. The gas sensor according to claim 1, in which the water-repelling filter and a sintered porous metal sheet are provided, in said order from outside, in a lead-in segment of the case.

3. The gas sensor according to claim 2, in which the sensing element is adapted to sense hydrogen, wherein the case is adapted to be disposed in an exit passage on a cathode side of a solid polymer membrane type fuel battery.

4. A gas sensor comprising:
a gas-sensing element comprising a catalyst;
a temperature-compensating element;
a case holding said elements;
a heater disposed between a specimen gas intake of the case and the gas-sensing and temperature-compensating elements at a point where the specimen gas intake is divided and a lead-in segment distributes the specimen gas to the sensing and temperature-compensating elements; and
a water-repelling filter disposed at the specimen gas intake of the case; wherein the concentration of a specimen gas is determined from the difference in electrical resistance between the gas-sensing element and the temperature-compensating element.

5. The gas sensor according to claim 4, in which the water-repelling filter and a sintered porous metal sheet are provided, in said order from outside, in the lead-in segment of the case.

6. The gas sensor according to claim 5, in which the sensing element is adapted to sense hydrogen, wherein the case is adapted to be disposed in an exit passage on a cathode side of a solid polymer membrane type fuel battery.

7. A gas sensor comprising:
a gas-sensing element comprising a catalyst;
a temperature-compensating element;
a case holding said elements;
a pair of heaters each having a heat-release surface extending along the direction in which the specimen gas flows such that the sensing and temperature-compensating elements are disposed between the paired heaters; and
a water-repelling filter disposed at the specimen gas intake of the case; wherein the concentration of a specimen gas is determined from the difference in electrical resistance between the gas-sensing element and the temperature-compensating element.

8. The gas sensor according to claim 7, in which the water-repelling filter and a sintered porous metal sheet are provided, in said order from outside, in a lead-in segment of the case.

9. The gas sensor according to claim 8, in which the sensing element is adapted to sense hydrogen, wherein the case is adapted to be disposed in an exit passage on a cathode side of a solid polymer membrane type fuel battery.

10. A gas sensor comprising:
a gas-sensing element comprising a catalyst;
a temperature-compensating element;
a case holding said elements;
a pair of heaters each having a heat-release surface extending along the direction in which the specimen gas flows disposed between the sensing and temperature-compensating elements so that the heat-release surfaces thereof face the sensing and temperature-compensating elements; and
a water-repelling filter disposed at the specimen gas intake of the case; wherein the concentration of a specimen gas is determined from the difference in electrical resistance between the gas-sensing element and the temperature-compensating element.

11. The gas sensor according to claim 10, in which the water-repelling filter and a sintered porous metal sheet are provided, in said order from outside, in a lead-in segment of the case.

12. The gas sensor according to claim 11, in which the sensing element is adapted to sense hydrogen, wherein the case is adapted to be disposed in an exit passage on a cathode side of a solid polymer membrane type fuel battery.

13. A gas sensor comprising:
a gas-sensing element comprising a catalyst;
a temperature-compensating element;
a case holding said elements;
a pair of heaters disposed between the sensing and temperature-compensating elements and fitted to a member that fastens said sensing and temperature-compensating elements; and
a water-repelling filter disposed at the specimen gas intake of the case; wherein the concentration of a specimen gas is determined from the difference in electrical resistance between the gas-sensing element and the temperature-compensating element.

14. The gas sensor according to claim 13, in which the water-repelling filter and a sintered porous metal sheet are provided, in said order from outside, in a lead-in segment of the case.

15. The gas sensor according to claim 14, in which the sensing element is adapted to sense hydrogen, wherein the case is adapted to be disposed in an exit passage on a cathode side of a solid polymer membrane type fuel battery.

* * * * *